United States Patent [19]

Fildes

[11] 4,001,389
[45] Jan. 4, 1977

[54] SLOW RELEASE BIOLOGICALLY ACTIVE MATERIALS FOR FEEDING TO RUMINANT ANIMALS

[75] Inventor: Francis James Thomas Fildes, Runcorn, England

[73] Assignee: Imperial Chemical Industries Limited, London, England

[22] Filed: Sept. 23, 1974

[21] Appl. No.: 508,715

[30] Foreign Application Priority Data

Sept. 26, 1973 United Kingdom ............. 45089/73

[52] U.S. Cl. .................................. 424/19; 424/32; 424/78
[51] Int. Cl.² ...................... A61K 9/22; A61K 9/32
[58] Field of Search ......................... 424/19, 32, 78

[56] References Cited

UNITED STATES PATENTS

| 3,492,398 | 1/1970 | Marco et al. | 424/32 |
| 3,880,990 | 4/1975 | Bauer | 424/19 |

Primary Examiner—Sam Rosen
Attorney, Agent, or Firm—Cushman, Darby & Cushman

[57] ABSTRACT

Biologically active compositions suitable for feeding to a ruminant animal containing a biologically active material coated with or in a matrix of a polymeric material having amide repeat units of the structure $$-NR_1-A-NR_1-CO-B-CO- \quad (I)$$

wherein the groups $R_1$, which may be the same or different, are hydrogen alkyl or substituted alkyl groups, and A and B are divalent groups one or both of which includes the group

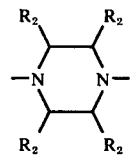
(II)

wherein the groups $R_2$, which may be the same or different, are hydrogen alkyl or substituted alkyl groups the proportion of nitrogen in the polymeric material derived from the amino groups in II being in the range of from 2% to 10% by weight of the polymeric material.

14 Claims, No Drawings

SLOW RELEASE BIOLOGICALLY ACTIVE MATERIALS FOR FEEDING TO RUMINANT ANIMALS

This invention relates to biologically active compositions suitable for feeding to ruminant animals.

Many biologically active materials are known which are useful in providing desirable effects when fed to ruminant animals, e.g. sheep, goats and cows. Such suitable biologically active materials include nutrients, antibiotics, sedatives, hormones, and growth promoting agents in general. To produce the desired effects the biologically active materials should be absorbed in the gastrointestinal tract after the material has passed through the rumen of the animal, for example, in the abomasum or in the intestine.

However, many biologically active materials when orally administered to ruminants are decomposed or otherwise adversely affected by the bacteria present in the rumen of the animal with the result that by the time the biologically active material is passed to the abomasum of the ruminant the biological activity of the material is considerably reduced or has even been destroyed completely. Furthermore, the biologically active material may destroy the bacteria in the rumen of the animal with consequent adverse effect on the animal's digestive capability.

It has been proposed to protect such biologically active materials so that during passage of the material through the rumen of the animal contact between the rumen fluids and the material is minimised, the protecting means being such as to be capable of being attacked by the fluids present in the abomasum of the ruminant with the result that the biologically active material is released in the abomasum and in the intestine.

The present invention provides a biologically active composition suitable for feeding to ruminant animals, the composition being sufficiently stable to result in at most only a slow release of the biologically active material when the composition is in contact with the fluids in the rumen of the animal yet being capable of releasing the biologically active material at a substantial rate when the composition is contacted with the abomasal fluids.

According to the present invention there is provided a biologically active composition suitable for feeding to a ruminant animal protected by a polymeric material, the polymeric material comprising amide repeat units having the structure $$-NR_1 - A - NR_1 - CO - B - CO - \quad \text{I}$$

where the groups $R_1$, which may be the same or different, are hydrogen or hydrocarbyl or substituted hydrocarbyl groups, and the units A and B are divalent groups one or both of which includes the piperazine group

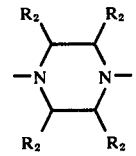

where the groups $R_2$, which may be the same or different, are hydrogen or hydrocarbyl or substituted hydrocarbyl groups, the proportion of nitrogen in the polymeric material derived from the amino groups in the group having structure II being in the range from 2% to 10% by weight of the polymeric material. Suitably, the groups $R_1$ and $R_2$ are hydrocarbyl groups.

One or both of the divalent groups A and B may include a group having the structure II. However, it is convenient for the latter group to be included in group A, that is, for the polymeric material to have the structure

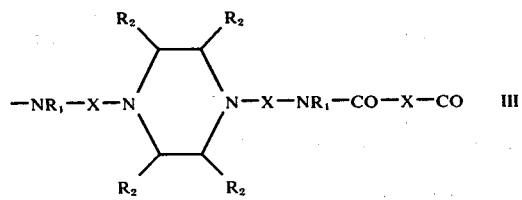

where the groups X, which may be the same or different, are hydrocarbyl groups.

The groups $R_1$ and $R_2$ when hydrocarbyl, may suitably be alkyl groups. However, for reasons of availability of starting compounds from which the polymeric material is prepared, the groups $R_1$ and $R_2$ conveniently are hydrogen.

Similarly, for reasons of availability of starting compounds from which the polymeric material is prepared, the groups X preferably are methylene, polymethylene or hydrocarbyl, preferably alkyl, derivatives of methylene or polymethylene.

Thus, the amide repeat units preferably have the structure

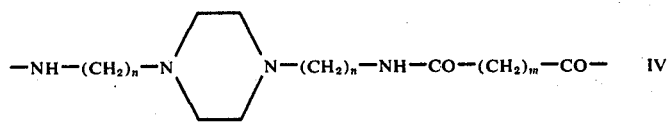

where n and m are whole numbers of at least one.

Stated in another way, the polymeric material would have amide repeat units having either the structure:

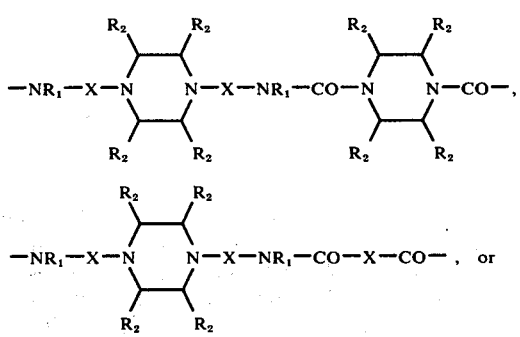

-continued

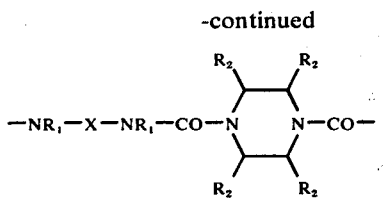

wherein the groups $R_1$, which may be the same or different, are hydrogen, or alkyl groups, the groups $R_2$, which may be the same or different, are hydrogen or alkyl groups and the groups X, which may be the same or different are selected from the group consisting of methylene, polymethylene and alkyl derivatives thereof, the proportion of nitrogen in the polymeric material derived from the amino groups in the piperazine groups being in the range of from 2% to 10% by weight of the polymeric material and the molecular weight of the polymeric material is such that the polymeric material has a reduced viscosity of at least 0.3 dl $g^{-1}$ when measured in a 1% by weight solution in methanol containing 5% by weight of lithium chloride at 25° C.

The polymeric material in the composition of the invention comprises amide units of the structure I. The polymeric material preferably contains at least 50% by weight of such units and is suitably a polyamide made up substantially completely of such units. However, it is not essential that the polymeric material be made entirely of such units. For example, the polymeric material may be a copolyamide which includes amide repeat units having structure I and which also include amide repeat units having a structure other than structure I. Alternatively, the polymeric material may be a polyesteramide possessing ester repeat units and amide repeat units some or substantially all of which amide units have the structure I.

Whatever may be the precise structure of the polymeric material it must include amide repeat units having the structure I, these amide units including at least one divalent group having the structure II in an amount such that the proportion of nitrogen in the polymeric material derived from the amino groups in Structure II lies in the range 2% to 10% by weight of the polymeric material.

In order to protect the biologically active material, the polymeric material in the biologically active composition may be in the form of a coating around the biologically active material. Alternatively, the biologically active material in the composition may be present in a matrix of the polymeric material.

In use the composition is administered orally to the ruminant animal. Where the polymeric material in the biologically active composition is in the form of a coating around the biologically active material, the coating is generally sufficiently impermeable to result in at most only a slow release of the biologically active material during the time that the composition is in the rumen and is in contact with the rumen fluids. When the composition is passed to the abomasum of the animal it is generally found that the coating is sufficiently permeable to the abomasal fluids to result in rapid release of the biologically active material. In an extreme case the abomasal fluids may dissolved the coating.

Where the biologically active composition is in the form of a biologically active material in a matrix of polymeric material the matrix is generally sufficiently stable in the rumen fluid to result in at most only a slow release of biologically active material in the rumen. When the composition is passed to the abomasum of the animal the abomasal fluids attack the polymeric material and break up the matrix with the result that there is, in general, a rapid release of the biologically active material.

With biologically active compositions outside the scope of the invention in which the proportion of nitrogen in the polymeric material derived from the amino groups in the group having structure II is less than 2% then, although the polymeric material may be sufficiently insensitive to the rumen fluids to prevent substantial release of the biologically active material in the rumen, the polymeric material is generally also relatively insensitive to the abomasal fluids with the result that at most only relatively slow release of the biologically active material in the abomasum is obtained.

On the other hand, with biologically active composition outside the scope of our invention in which the proportion of nitrogen in the polymeric material derived from the amino groups in the group having structure II is greater than 10% then, although the polymeric material may be sufficiently sensitive to the abomasal fluids such that a substantial rate of release of the biologically active material in the abomasum is obtained, the polymeric material is also, in general, sensitive to the rumen fluids with the result that, due to inadequate protection of the biologically active material when the composition is in the rumen, a substantial rate of release of the biologically active material in the rumen is obtained.

In order that the polymeric material should provide substantial protection for the biologically active material when the composition is in the rumen it is preferred that in the composition of the invention the proportion of nitrogen in the polymeric material derived from the amino groups in the group having structure II is not greater than 8% by weight of the polymeric material, and is more preferably in the range 4% to 8% by weight of the polymeric material.

Thus, where the polymeric material in the composition is the preferred polymeric material consisting of repeat units having the structure IV, that is,

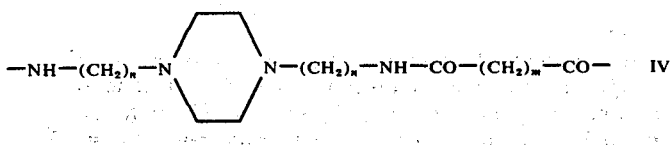

and where the proportion of nitrogen in the polymeric material derived from the amino groups in the group having the structure II is in the range 4% to 8% by weight of the polymeric material, then in the repeat unit the value of $2n + m$ should be in the range 13 to 38. For example, in the repeat unit having structure IV where n is 3, m is preferably in the range 7 to 32 e.g. 8, 10, 12 or 14, and where n is 5, m is preferably in the range 3 to 28.

The biologically active composition may be in any form suitable for oral administration, e.g. in the form of a tablet, pellet, pilule, pill, or granule.

It is preferred that the biologically active material in the composition is protected by means of a coating of polymeric material.

One method of applying the coating involves rotating a bed of tablets, pellets, granules, pilules or the like, of the biologically active material in a coating pan and applying to the moving tablets or the like a solution of dispersion of the polymeric material in a suitable diluent. Care should be taken that each tablet or the like is coated with polymeric material. Care should also be taken to avoid agglomeration of tablets or the like. The coated tablets or the like may be dried by exposure to warm air and in order that the diluent may readily be removed it is preferred to use a low boiling diluent, e.g. methanol, in which the polymeric material is soluble.

The coating procedure is continued until the desired thickness of coating is achieved.

Where the biologically active composition carries a protective coating of polymeric material the thickness of the coating will have a bearing on the stability of the coating when in the rumen and on the sensitivity of the coating to the abomasal fluids. Thus, in general, the greater the thickness of the coating the greater the stability of the coating when in the rumen, and the greater the degree of protection afforded to the biologically active material by the coating, and also the less the sensitivity of the coating to the abomasal fluids. For a coating of a given polymeric material the thickness of the coating should be chosen to give the desired degree of protection in the rumen and the desired degree of sensitivity to the abomasal fluids.

The polymeric material may be prepared by condensing in substantially equimolar proportions at least one diamine having the structure $NHR_1 - A - NHR_1$, or amide-forming derivative thereof, and at least one diacid having the structure $HOOC - B - COOH$, or amide-forming derivative thereof, optionally together with other polycondensable materials, where $R_1$ is as hereinbefore described and the units A and B are divalent groups one or other or both of which includes the group having the structure

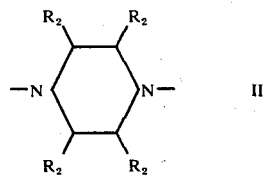

II where $R_2$ is as hereinbefore described, the diamine and diacid, or amide forming derivatives thereof, being selected to provide a proportion of nitrogen in the polymeric material derived from the amino groups in the group having the structure II in the range 2% to 10% by weight of polymeric material.

The groups $R_1$ and $R_2$ which may be, for example, substituted hydrocarbyl, should not contain atoms or groups which prevent polycondensation of the diamine and the diacid or amide-forming derivatives thereof.

The polymeric materials may be made by techniques well-known in the art of polycondensation technology.

The molecular weight of the polymeric material is desirably such that the material has a reduced viscosity of at least 0.3 dl g$^{-1}$ when measured in a 1% solution in methanol containing 5% by weight of lithium chloride at 25° C.

The invention is now illustrated by the following Examples in which all parts are expressed as parts by weight.

EXAMPLE 1

Preparation of a polyamide from N,N'-bis(3-aminopropyl) piperazine and dodecanedioic acid by melt condensation.

20 Parts of dodecanedioic acid was dissolved by warming in 87 parts of absolute ethanol. After cooling, a solution of 17.8 parts of N,N'-bis(3-aminopropyl) piperazine in 40 parts of absolute ethanol was added to the solution. Mixing was accompanied by a vigorous exotherm and as the hot mixture cooled, crystals of the amide salt were formed. The crystals were filtered off, washed with ethanol and dried under vacuum.

20 parts of the crystalline amide salt were charged to a glass polymerisation tube fitted with a nitrogen inlet and an air condenser. The tube was purged with nitrogen and then heated on a sand bath to 200° C, at which temperature the salt melted. The tube was then evacuated to a pressure of 0.1 mm of mercury absolute and the temperature was raised to 270° C. After heating for 3 hours at 270° C, th tube was allowed to cool to room temperature and the polyamide was removed from the tube. The reduced viscosity of a 1% by weight solution of the polyamide in methanol containing 5% by weight lithium chloride at 25° C was 0.87 dl gm$^{-1}$.

EXAMPLE 2

Preparation of a polyamide from N,N'bis(3-aminopropyl) piperazine and dodecanedioic acid chloride by interfacial condensation.

7.52 Parts of freshly distilled dodecanedioic acid chloride was dissolved in 320 parts of carbon tetrachloride and a solution of 14.2 parts of N,N'-bis(3-aminopropyl) piperazine in 100 parts of distilled water was added. The mixture was gently agitated by hand and the polyamide which formed at the interface between the two solutions was removed by filtration. The excess solution was pressed out of the polyamide and the polyamide was then thoroughly washed with distilled water and dried under vacuum. The reduced viscosity of a 1% by weight solution of the polyamide in methanol at 25° C was 0.45 dl gm$^{-1}$.

EXAMPLE 3

Coating of tablets containing quinoxaline di-N-oxide with the polyamide prepared in Example 1.

50 Parts of biconvex tablets containing quinoxaline di-N-oxide was charged to a glass coating pan which was heated by means of an infra-red lamp. The pan was rotated and 50 parts of a 10% w/v methanol solution of the polyamide prepared in Example 1 was added to the tumbling tablets in aliquots of about 2 parts. The methanol was allowed to evaporate before the next aliquot was added. When all the solution had been added the coated tablets were recovered. The coating of the polyamide comprised about 10 weight percent of the total weight of the coated tablet.

EXAMPLE 4

A tablet containing 0.150 part of quinoxaline di-N-oxide which had been coated following the procedure described in Example 3 with a polyamide prepared as described in Example 1 was placed in a gauze tissue container and the container was immersed in 400 mls of distilled water in a 1 liter blackened conical flask, the distilled water simulating rumen fluid. The temperature was maintained at 37° C and the water was stirred at 60 r.p.m.

Thereafter, 5 ml. samples were removed from the flask and the concentration of quinoxaline di-N-oxide in the solution was estimated by measuring the intensity of the ultra-violet absorption band at 290 m$\mu$. After 24 hours the amount of quinoxaline di-N-oxide released from the coated tablet was less than 5% of the original amount in the tablet.

After 24 hours the distilled water was acidified and buffered at pH4 in order to simulate abomasal fluid by adding tablets of a phosphate buffer to the solution. The amount of quinoxaline di-N-oxide released at pH4 was again estimated by ultra violet spectrophotometry 3 hours after acidification, all the quinoxaline di-N-oxide present in the coated tablet had been released into the acidified solution.

EXAMPLE 5

A tablet containing 0.150 part of quinoxaline di-N-oxide which had been coated following the procedure described in Example 3 with a polyamide prepared as described in Example 1 was placed in a gauze tissue container and the container was immersed in 300 mls of rumen fluid. The fluid had been removed from the rumen of a slaughtered animal. The rumen fluid was used in the experiment immediately after removal from the animal in order to minimise the effect of deterioration of the rumen fluid. The fluid was maintained at a temperature of 37° C and stirred at 60 r.p.m.

Periodically, 10 ml samples of the rumen fluid were removed and the amount of quinoxaline di-N-oxide in the samples was assayed as follows. 30 mls. of a 10% aqueous solution of trichloracetic acid was added to the rumen fluid in a test tube covered with silver foil and the mixture was centrifuged for 5 minutes. 25 Mls of the supernatant liquid was charged to a foil covered test tube and 5 mls of 10N sodium hydroxide was then added with shaking. 2 mls of a 20% w/v aqueous sodium dithionite solution was then added and the mixture was allowed to stand for 10 minutes. 10 mls of chloroform was then added to the solution and the mixture was shaken for two minutes. An aliquot of the chloroform layer was then transferred from the test tube to an ultra-violet spectrometer cell and the amount of quinoxaline formed as a result of the reduction of the quinoxaline di-N-oxide, was estimated from the intensity of the absorption band at 313 m$\mu$.

After 48 hours in rumen fluid 4% of the quinoxaline di-N-oxide in the coated tablet had been lost. The tablet was then removed from the fluid and immediately transferred to a bath containing distilled water, acidified and buffered to pH4 with phosphate buffer. The contents of the bath were stirred at 60 r.p.m. at 37° C. After 4 hours in this bath, all the quinoxaline di-N-oxide in the tablet had been released.

EXAMPLE 6

Preparation of copolyamides from N,N'-bis(3 aminopropyl) piperazine, hexamethylene diamine and dodecanedioic acid by melt condensation.

The salt of N,N'-bis(3-aminopropyl) piperazine and dodecanedioic acid (salt A) was prepared as in Example 1. The salt of hexamethylene diamine and dodecanedioic acid (salt B) was prepared by dissolving 23 parts of dodecanedioic acid in 110 parts of absolute ethanol and adding to it a solution of 11.8 parts of hexamethylene diamine in 50 parts of absolute ethanol. Mixing was accompanied by an exothermic reaction and crystals of the amide salt were precipitated on cooling. These crystals were filtered off, washed with ethanol and dried under vacuum.

A series of copolyamides was prepared by reacting various mixtures of the salts A and B as in Example 1, to yield copolyamides containing the amounts of nitrogen derived from the amino group in the group having the structure II, shown in the Table:-

| Parts Salt A | Parts Salt B | % amine N in copolymers |
| --- | --- | --- |
| 50.0 | 0 | 7.1 |
| 50.0 | 2.2 | 6.8 |
| 55.9 | 5.0 | 6.5 |
| 50.8 | 10.0 | 5.9 |
| 58.8 | 20.0 | 5.3 |
| 60.0 | 48.3 | 3.9 |

All the copolymers were hard materials of high molecular weight.

EXAMPLE 7

20 parts of succinic anhydride was dissolved in 800 parts of a 1:1 mixture of chloroform and methanol and the solution was cooled in ice. A solution of 20 parts of N,N'bis-(3-aminopropyl) piperazine in 50 parts of the same solvent mixture was cooled, and the solution was added slowly to the solution of succinic anhydride. The mixture was allowed to stand at room temperature for one hour and then the solvent was removed on a rotary evaporator to yield a buff-coloured slurry. On standing, the slurry solidified into buff-coloured crystals which then were washed with pentane and ethanol, and then dried at room temperature under vacuum. The dry product was analysed by elemental analysis and end-group analysis, and was shown to be 2:1 diamide of succinic anhydride and N,N'bis(3-aminopropyl) piperazine.

10 parts of the diamide was heated under nitrogen at 180° C with 2.09 parts of hexamethylene diamine. When the mixture had melted, a vacuum was applied and heating was continued for 5 hours. The product was a waxy, red solid which was soluble in water.

The diamide was also polymerized in a separate experiment with nonane diamine. 10 parts of the diamide was heated under nitrogen at 240° C with 2.84 gms of 1.9 diamino-nonane. Heating was continued under vacuum for 5 hours. On subsequent cooling, the mixture solidified to a red-brown solid which was insoluble in water.

Both products had low reduced viscosities, indicating low molecular weight.

EXAMPLE 8

Preparation of a polymer matrix containing a biologically active material.

1 part of the polyamide prepared in Example 1 was dissolved in 10 parts of methanol, and 1 part of quinoxaline di-N-oxide was suspended in the solution. The mixture was quickly added to 100 parts of petroleum ether and the solid which formed was filtered off and dried under vacuum. The solid was then compressed at 30 tons pressure between two metal plates heated to 125° C in a hydraulic press, to yield a shiny, hard plaque. This plaque was cut into small pieces and the release of the drug at pH 7 was measured spectrophotometrically as in Example 4. After 24 hours in a medium pH 7, only 10.3% of the drug had been released. The solution was acidified to pH 4 and 60% of the drug was released within 2.5 hours.

EXAMPLE 9

Spheronized granules containing oxytetracycline dihydrate were prepared as follows:-

15 parts of oxytetracycline dihydrate and 15 parts of microcrystalline cellulose (Avicel) were mixed on a planetry mixer and the mixture was then damped with 70 parts of water. The wet mass was rubbed through a 10-mesh screen and the resultant granules were spheronized on a rotating plate spheronizer. The spheres were then dried and sieved into fractions of narrow size distribution.

20–30 mesh size granules were coated with the polyamide prepared in Example 1 by a proceedure similar to that described in Example 3. The polymer was applied to the spheres at room temperature as a 2.5% solution in a 1:1 mixture of methylene chloride and methanol until the coating comprised about 5% by weight of the total weight of the coated granules.

The rate of release of the oxytetracycline dihydrate from the coated spheres was measured spectrophotometrically as described in Example 4. The release was monitored by measuring the intensity of the absorption spectrum of the released drug at 275 millimicrons. After 24 hours at pH 7, less than 5% by weight of the encapsulated drug had been released, but when the solution was acidified to pH 4, the coating quickly dissolved and the drug was released.

Similarly, less than 5% by weight of the encapsulated drug was released from the coated spheres in 24 hours when they were incubated at 37° C with rumen fluid, freshly removed from a slaughtered cow. This demonstrates that the coating is resistant to attack by the organisms present in the rumen contents and would protect the drug during its residence in the rumen.

EXAMPLE 10

Two one-year-old calves (one heifer and one bullock) were prepared for the trial by surgically forming a fistulla through into the rumen. The trial measured the release of quinoxaline di-N-oxide into the rumen and into the blood of the calves. Uncoated tablets and polymer coated tablets were compared, using the tablets described in Example 3.

2 gms of quinoxaline di-N-oxide in the form of 50 × 40 mgm tablets were inserted via the rumen fistulla into each animal. Samples of rumen fluid and samples of blood from the jugular vein of each animal were removed periodically and analysed for quinoxaline di-N-oxide using the method described in Example 5.

After an appropriate period, 5 gms of polymer coated tablets were inserted into each animal via the fistulla and rumen fluid and blood samples were removed as before. The concentration of quinoxaline di-N-oxide in the rumen fluids and in the blood in the two experiments is shown in the following Table:-

| Time after dosing (hours) | Conc$^n$ drug in ($\mu$g/ml) Cow A | Cow B | Conc$^n$ drug in blood ($\mu$g/ml) Cow A | Cow B |
|---|---|---|---|---|
| UNCOATED TABLETS | | | | |
| 3 | 5.4 | 6.2 | 0.02 | 0 |
| 5 | 1.0 | 1.4 | 0.06 | 0 |
| 23 | 0.5 | 0.4 | 0 | 0 |
| 27 | 0.3 | 0.25 | 0 | 0 |
| 29 | 0.3 | 0.23 | 0 | 0 |
| 47 | 0 | 0 | 0 | 0 |
| COATED TABLETS | | | | |
| 3 | 0.73 | 0.04 | 0 | 0 |
| 6 | 0.45 | 0.02 | 0 | 0 |
| 22 | 0.44 | 0.32 | 0.81 | 0.88 |
| 26 | 0.22 | 0.63 | 0.55 | 0.33 |
| 30 | 0.26 | 0.30 | 0.79 | 0.21 |
| 46 | 0.06 | 0.09 | 0.17 | 0.19 |
| COATED TABLETS | | | | |
| 50 | 0.03 | 0.04 | 0.17 | 0.17 |
| 54 | 0.02 | 0.02 | 0.14 | 0.13 |
| 70 | 0 | 0 | 0.11 | 0 |
| 75 | 0 | 0 | 0 | 0 |
| 78 | 0.09 | 0.02 | 0 | 0 |

These results show that with the uncoated tablets the drug was rapidly released into the rumen and was not made available for absorption into the blood. However, the polyamide coated tablets released very little drug into the rumen but released the compound subsequent to residence in the rumen and significant blood levels were measured. This demonstrates that the coating afforded protection to the tablets in the rumen but must have dissolved in the acidic regions of the gastrointestinal tract to release the drug for absorption into the blood.

What I claim is:

1. A biologically active composition suitable for feeding to a ruminant animal comprising a biologically active material coated with or in a matrix of a polymeric material, the polymeric material comprising amide repeat units having the structure

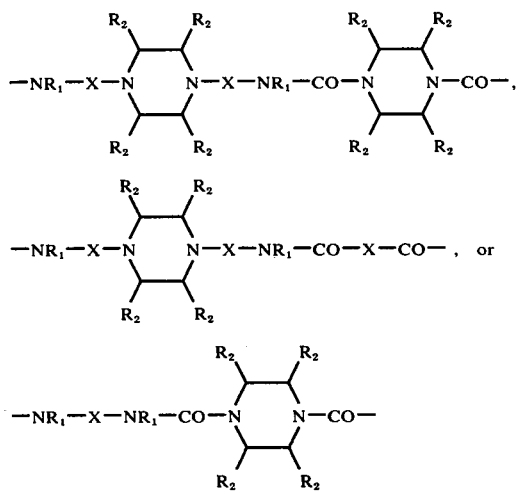

wherein the groups $R_1$, which may be the same or different, are hydrogen, or alkyl groups, the groups $R_2$, which may be the same or different, are hydrogen or alkyl groups and the groups X, which may be the same or different are selected from the group consisting of methylene, polymethylene and alkyl derivatives thereof, the proportion of nitrogen in the polymeric material derived from the amino groups in the piperazine groups being in the range of from 2% to 10% by weight of the polymeric material and the molecular weight of the polymeric material is such that the polymeric material has a reduced viscosity of at least 0.3 dl g$^{-1}$ when measured in a 1% by weight solution in methanol containing 5% by weight of lithium chloride at 25° C.

2. A composition as claimed in claim 1 wherein the polymeric material comprises amide repeat units having the structure

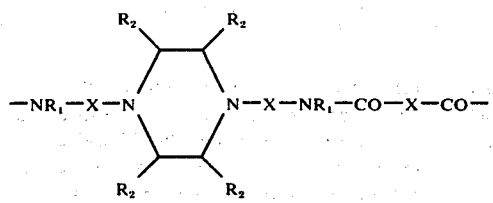

3. A composition as claimed in claim 2 wherein the groups X are methylene groups or alkyl derivative thereof.

4. A composition as claimed in claim 2 wherein the groups X are polymethylene groups or alkyl derivatives thereof.

5. A composition as claimed in claim 1 wherein the groups R$_1$ are hydrogen.

6. A composition as claimed in claim 1 wherein the groups R$_2$ are hydrogen.

7. A composition as claimed in claim 6 wherein the repeat unit of the polymeric material has the structure

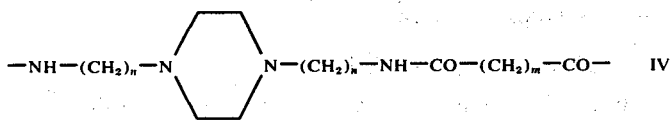

wherein n and m are integers of at least one.

8. A composition as claimed in claim 7 wherein 2n+m is in the range 13 to 38.

9. A composition as claimed in claim 1 wherein the proportion of nitrogen in the polymeric material derived from the amino groups in the piperazine groups is not greater than 8% by weight of the polymeric material.

10. A composition as claimed in claim 9 wherein the proportion of nitrogen is from 4% to 8% by weight of the polymeric material.

11. A composition as claimed in claim 1 wherein the polymeric material is the condensation product of N,N'-bis(3-aminopropyl) piperazine and dodecanedioic acid or dodecanedioic acid chloride.

12. A composition as claimed in claim 1 wherein the polymeric material is in the form of a coating on the biologically active material.

13. A composition as claimed in claim 1 which is in the form of a tablet or pill.

14. A composition according to claim 1 wherein said biologically active material is selected from the group consisting of nutrients, antibiotics, seditives, hormones, and growth promoting agents.

* * * * *